United States Patent [19]

Farr et al.

[11] Patent Number: 5,026,384
[45] Date of Patent: Jun. 25, 1991

[54] ATHERECTOMY SYSTEMS AND METHODS

[75] Inventors: Andrew F. Farr, Spring Valley; Herbert R. Radisch, Jr., San Diego, both of Calif.

[73] Assignee: InterVentional Technologies, Inc., San Diego, Calif.

[21] Appl. No.: 433,032

[22] Filed: Nov. 7, 1989

[51] Int. Cl.⁵ ............................................. A61B 17/32
[52] U.S. Cl. .................................. 606/159; 606/172; 606/180
[58] Field of Search ...................... 606/159, 167–169, 606/170–173, 180–181

[56] References Cited

U.S. PATENT DOCUMENTS

| | | | |
|---|---|---|---|
| 4,672,965 | 6/1987 | Baum | 606/172 X |
| 4,887,613 | 12/1989 | Farr et al. | 606/159 |
| 4,895,166 | 1/1990 | Farr et al. | 606/159 X |

Primary Examiner—Richard J. Apley
Assistant Examiner—Jennifer L. Doyle
Attorney, Agent, or Firm—Nydegger & Associates

[57] ABSTRACT

An atherectomy system includes a guide wire which can be inserted into an artery of a patient to a region of occlusion, a torque tube having a cutter device affixed to its distal end which is insertable into the artery over the guide wire, and a protective support sheath surrounding the guide wire and the torque tube. A retraction device controllably retracts the support sheath so as to allow the cutter on the distal end of the torque tube to extend progressively greater distances beyond the distal end of the support sheath. The system also includes means for rotating the torque tube, thereby simultaneously rotating the cutter, and vacuum means connected to the torque tube for extracting dislodged cuttings from the patient's bloodstream. The guide wire is preferably provided with an abutment on its distal end which both mechanically limits the distance the cutter can advance into the patient's body and assists in retrieving the cutter from the patient's body following the atherectomy operation.

25 Claims, 5 Drawing Sheets

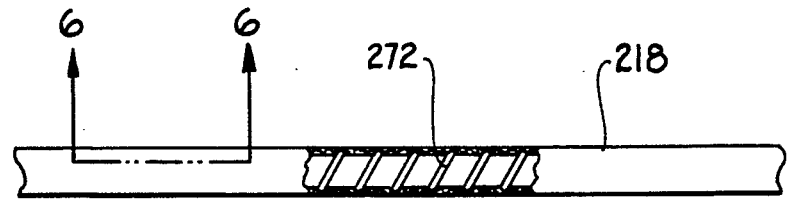
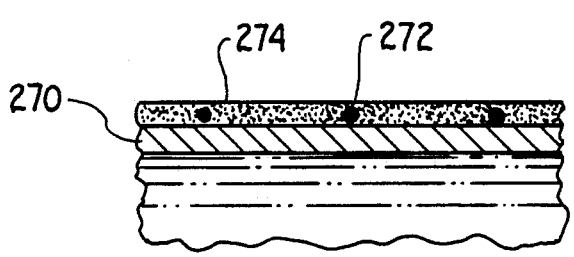
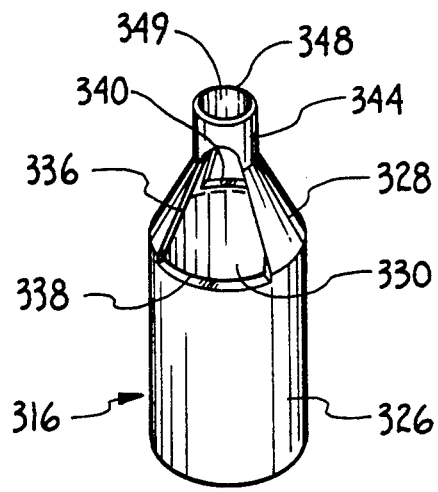
Fig. 7
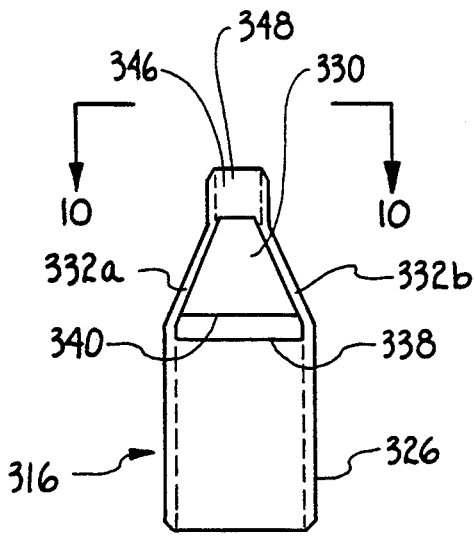
Fig. 9
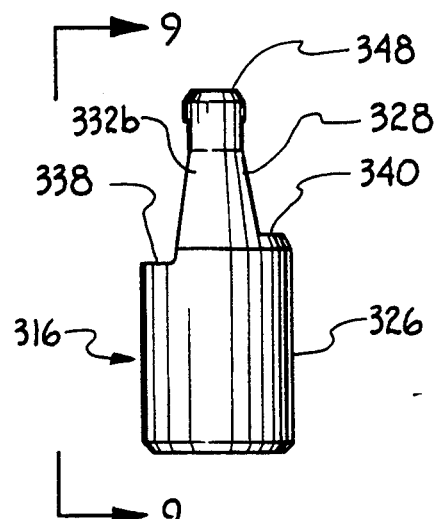
Fig. 8

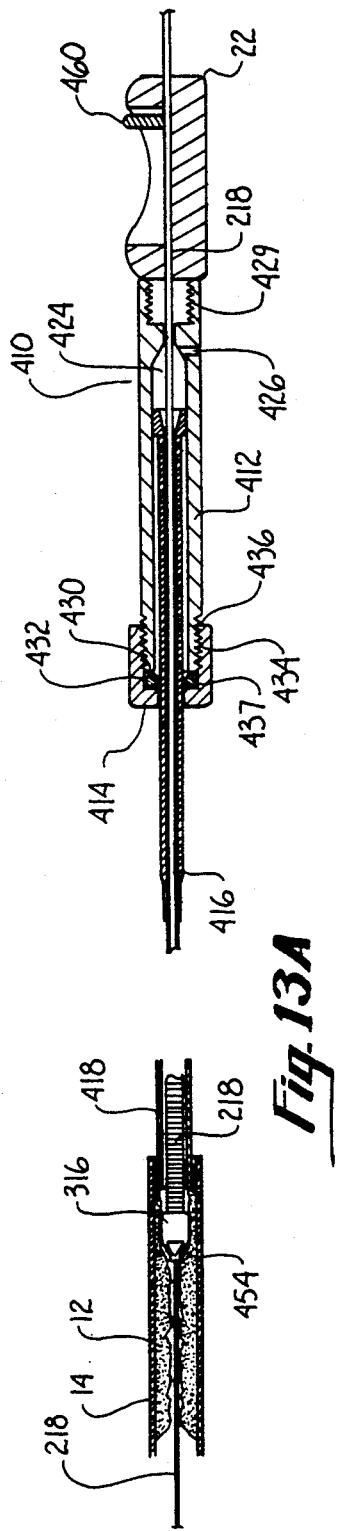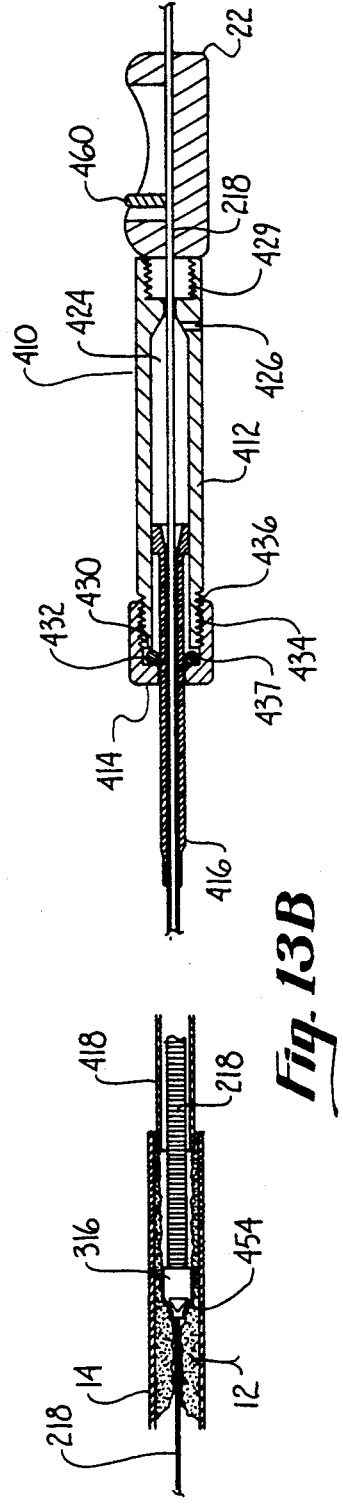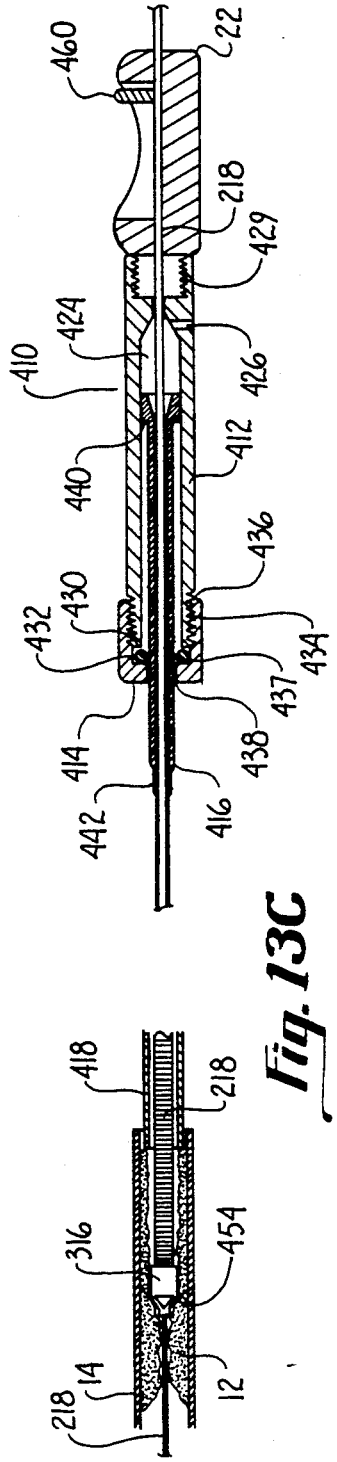

ATHERECTOMY SYSTEMS AND METHODS

FIELD OF THE INVENTION

This invention relates to systems and methods for excising obstructive matter from arteries and other lumens of living beings. More particularly, the invention relates to such systems and methods useful in performing atherectomy procedures.

BACKGROUND OF THE INVENTION

Heart attacks constitute one of the major sources of incapacitation or death to human beings. Such failures often result from blockages in coronary arteries that are due to the accumulation of plaque on the arterial walls. Such accumulations of plaque gradually block the flow of blood through the arteries to the heart until there is a complete stoppage or almost a complete stoppage in the flow.

In addition to the problems incurred by blockages in coronary arteries, blockages of other arteries can also cause incapacitation or death to human beings. Plaque buildup in the arteries of the arms or legs can result in limb amputations. Plaque buildup in the arteries of the head and neck can result in strokes. Plaque buildup in the arteries of the kidneys can result in hypertension (high blood pressure). Additionally, plaque buildup in other peripheral (non-coronary) arteries can result in degradation of the organs which they supply.

Until relatively recently, it has been difficult to diagnose and detect the accumulation of plaque in the arteries of living beings. In recent years, techniques have been devised for detecting and locating accumulations of plaque on the arterial walls of living beings. Indeed, these techniques have become so advanced that it is now not uncommon to advance probes completely through the arteries to locate and estimate the relative amount of arterial blockage at such progressive positions along the artery.

Several techniques have also been developed to correct for blockages in the arteries of living beings. One well known technique which is often used is the so-called bypass surgery. In bypass surgery, the blocked portion of an artery is shunted using a segment of a vessel from another part of the body of the afflicted human being.

Bypass operations, however, can be of considerable danger to the living being undergoing the operation. One reason for this concern is that the living being has to be cut open to expose and treat the diseased site. The patient also has to undergo anesthesia, the effects of which are often unpredictable. Together, the trauma resulting from the anesthesia and the opening of the body of the living being presents a grave danger to the patient.

Angioplasty techniques have also been developed in recent years as a means to alleviate blockages in the arteries in living beings. As is well known, angioplasty procedures involve the insertion of a deflated balloon into the artery of the living being. The balloon is then moved, as by a conduit, to the blocked position. Thereafter, the balloon is inflated to expand the diameter of the artery and enlarge the passageway through the artery. In this manner, the plaque is at least partially broken up to thereby alleviate the blockage.

Angioplasty procedures, however, have certain inherent disadvantages. First, expansion of the arterial wall at the blocked position stretches, and thereby weakens, the arterial wall. This alone may cause adverse consequences. Further, since plaque blocking the artery is often calcified and quite hard, it can be difficult, and sometimes impossible, for the balloon to overcome the counterforce exerted by the plaque against the balloon. Still further, and very importantly, angioplasty procedures do not remove plaque from the artery. This is particularly troublesome since the obstructive tissue which remains in the artery creates a condition conducive to the creation of another blockage. Thus, it can be a recurring problem. Importantly, unlike angioplasty, atherectomy procedures cut the plaque, or other obstructive tissue, from the inside of the artery to create a passageway through the plaque. No expansion of the arterial wall is required.

As can be easily appreciated, not only must the atherectomy system employed be effective in cutting and removing plaque, it is essential during such a procedure that the cutting device be carefully controlled and not be allowed to cut through the arterial wall. For the present invention, the necessary control is provided by the concerted effort of a control unit which operatively positions the cutting device within a support sheath and a guide wire which establishes the path of the cutting device.

Several examples of guide wires have been previously disclosed. Typical of these examples are U.S. Pat. No. 3,731,671 which issued to Mageoh for an invention entitled "Low-Friction Catheter Guide" and U.S. Pat. No. 3,789,841 which issued to Antoshkiw for an invention entitled "Disposable Guide Wire." Further, the use of a guide wire for a rotary catheter system has been disclosed in U.S. Pat. No. 4,732,154 which issued to Shiber. All of these guide wires, however, are intended to do no more than provide a means to position the operative medical device over the positioned guide wire.

SUMMARY AND OBJECTS OF THE INVENTION

In view of the foregoing, it is a primary object of the present invention to provide an atherectomy system and method which effectively and controllably cuts a passageway through obstructive tissue in an artery.

A related object of the present invention is to provide an atherectomy system having means for accurately controlling the extent to which the cutting device extends into the area of obstruction in an artery.

A still further object of the present invention is to provide an atherectomy system having a steerable guide wire which mechanically limits the distance the atherectomy cutter device can advance into the body of a patient and which can also assist in retrieving the cutter device from the patient's body following the atherectomy operation.

Yet another object of the present invention is to provide an atherectomy system and method which is easy to use and which is cost-effective.

Consistent with the foregoing objectives, this invention provides an atherectomy system and method. The system comprises: a guide wire which can be inserted through an artery of a patient and into a region of occlusion; a torque tube having a rotatable cutter device affixed to its distal end which is insertable into the artery over the guide wire; and a protective support sheath surrounding the guide wire and the torque tube. The system further comprises means for controllably extending the cutter through the protective support sheath to allow the cutter at the distal end of the torque tube to extend progressively greater distances beyond the distal end of the support sheath. Additionally, the system includes means for rotating the torque tube so as to simultaneously rotate the cutter device, and vacuum means connected to the torque tube for extracting dislodged cuttings and debris from the patient's bloodstream.

The guide wire of the atherectomy system of the present invention preferably comprises a main shaft that is tapered at its distal end to form a flat ribbon. Such ribbon establishes a biased direction for bending the distal end of the guide wire. A flexible radiopaque coil is provided which surrounds and covers the ribbon and part of the tapered portion of the main shaft immediately proximal to the ribbon. Integrally attached to the distal end of the ribbon is a ball-shaped abutment. In combination with the main shaft, the abutment prevents movement of the torque tube and cutter beyond the point where the cutter makes contact with the abutment.

The torque tube of the atherectomy system of the present invention has strong and resilient properties such that it can be easily and efficiently inserted into the artery over the guide wire and manipulated to the position in the artery at which plaque is blocking the passage of blood in the artery. The torque tube thus follows the contour of the patient's artery and is able to communicate both a penetrating force for advancing the cutter along the guide wire and a torque for rotating the cutter. Thus, by rotating the torque tube manually or by a motor, the cutter attached to the distal end of the torque tube may be advanced against an arterial blockage by a physician to excise plaque from the arterial walls. The system then efficiently removes the excised plaque fragments, as by a vacuum, through the torque tube. In this way, potential danger caused by leaving excised plaque fragments in the bloodstream is eliminated.

In operation, the cutter attached to the torque tube must be exposed and extended beyond the distal end of the protective support sheath in order to effectively drill through obstructive tissue in an artery. Accordingly, means are provided to controllably extend the cutter for its operation.

In one preferred embodiment, the aforesaid extension means comprises a tubular insert which is attached to the proximal end of the protective support sheath and telescopically received within a substantially cylindrical housing. The support sheath is positioned within the artery of a patient and the cutter is initially positioned slightly beyond the distal end of the sheath and held in a fixed relationship with the support sheath. The cutter is then positioned against the tissue to be removed and is thereafter rotated and advanced through the obstructive tissue until the relationship between torque tube length and support sheath length prevents further advancement of the cutter. To continue drilling through the obstructive tissue, the tubular insert of the telescopic retraction means is incrementally retracted into the housing which effectively shortens support sheath length. Consequently, the cutter can be extended further beyond the distal end of the sheath a distance equal to the amount the insert is withdrawn into the housing. The rotating cutter is then advanced through the obstructive tissue until the relationship between torque tube length and telescopically shortened support sheath length prevents further advancement of the cutter.

These procedures are repeated until an effective passageway has been established through the obstructive tissue.

The novel objects and features of this invention, as well as the invention itself, both as to its structure and its operation, will be best understood from the accompanying drawings, taken in conjunction with the accompanying description and appended claims.

BRIEF DESCRIPTION OF THE DRAWINGS

FIG. 5 is an enlarged fragmentary view, partially broken to indicate elements in section, of one presently preferred embodiment of the torque tube of the atherectomy system of the present invention;

FIG. 6 is an enlarged fragmentary sectional view taken substantially on the lines 6—6 of FIG. 5 and illustrating certain components in the torque tube in further detail;

FIG. 7 is an enlarged perspective view of one presently preferred embodiment of the cutter of the atherectomy system of the present invention;

FIG. 8 is an enlarged elevational view of the cutter shown in FIG. 7;

FIG. 9 is an enlarged sectional view, taken on the lines 9—9 of FIG. 7, of the cutter shown in FIGS. 7 and 8 and schematically illustrates additional details of construction of the cutter;

FIGS. 13A, 13B and 13C are cross-sectional views of the cutter and the associated support sheath of the atherectomy system of the present invention illustrating the advancement of the cutter as it drills through obstructive tissue in an artery.

DESCRIPTION OF THE PREFERRED EMBODIMENT

It will be readily appreciated that the components of the present invention, as generally described and illustrated in the figures herein, could be arranged and designed in a wide variety of different configurations. Thus, the following more detailed description of one embodiment of the system and method of the present invention, as represented in FIGS. 1 through 13, is not intended to limit the scope of the invention, as claimed, but it is merely representative of one presently preferred embodiment of the invention.

Figure 1:
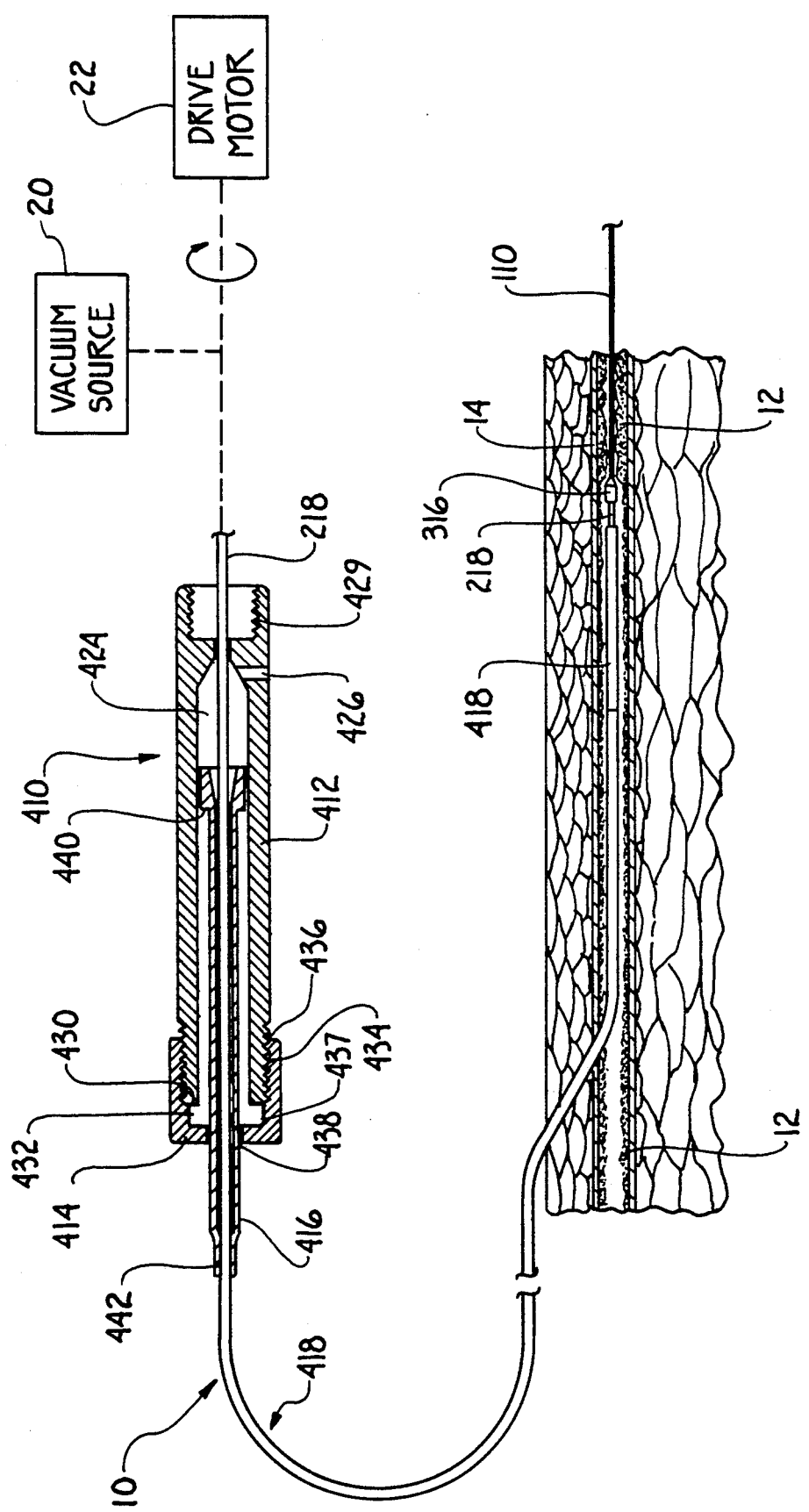
FIG. 1 is a schematic view, partially in section as to the mechanical features and partially in block form as to the electrical features, showing one presently preferred embodiment of the atherectomy system of the present invention.

Referring first to FIG. 1, the atherectomy system of the present invention, generally designated at 10, is useful for excising obstructive tissue such as plaque 12 from the lumen of an artery 14 in a living being. In one presently preferred embodiment, the system includes, as shown, a guide wire generally indicated at 110, a cutter generally indicated at 316, a torque tube generally indicated at 218, a protective support sheath generally indicated at 418, a support sheath control unit generally indicated at 410, and a vacuum source 20. The system may also include a motor 22 for rotating torque tube 218 and cutter 316 at a relatively low speed to excise the plaque 12 from artery 14.

Guide wire 110 of atherectomy system 10 primarily assists in properly positioning the components of system 10 within an artery 14 of a patient. Guide wires are extremely helpful during the insertion of a catheter or other medical device into the deeper recesses of a patient's body. This is so because the medical device itself usually lacks the steerability necessary for proper placement. Where extensive insertion of a medical device into a body is necessary for its proper placement, as is often the case with atherectomy devices, these disadvantages are profound An atherectomy operation is perhaps best accomplished if cutter 316 can be advanced with atherectomy torque tube 218 into a patient over a prepositioned guide wire 110. It may also be helpful if guide wire 110 will mechanically limit the distance to which cutter 316 can be inserted into the patient's body, i.e. not allow cutter 316 to extend beyond the distal end of guide wire 110. Further, it is advantageous if guide wire 110, when withdrawn from the patient's body, can be used to retrieve torque tube 218 and cutter 316 which it has guided into the operational location in the body.

Figure 2:
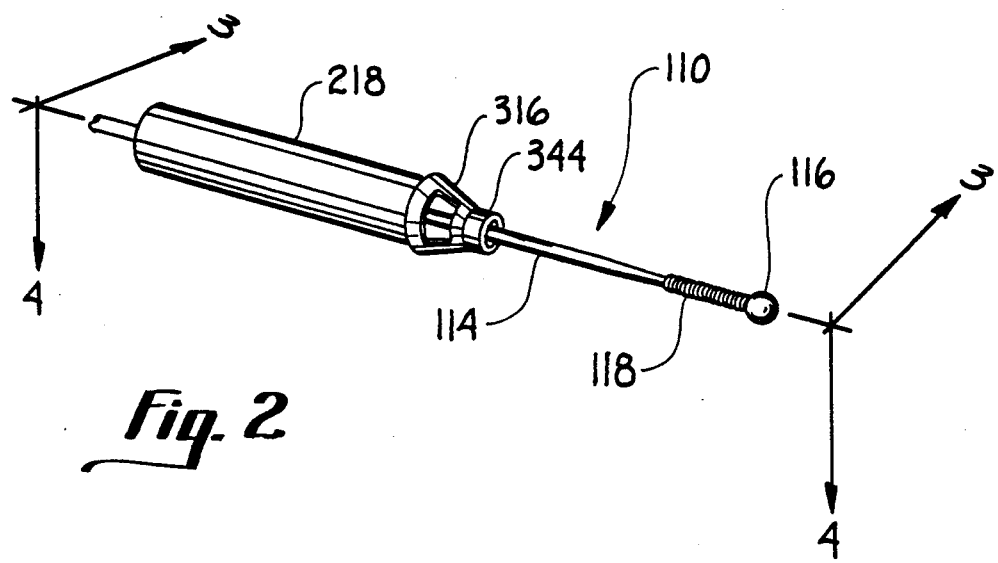
FIG. 2 is a partial perspective view of one presently preferred embodiment of the guide wire of the atherectomy system of the present invention shown in cooperative engagement with the torque tube and cutter.

Referring now to FIG. 2, one presently preferred embodiment of the guide wire 110 of atherectomy system 10 is shown in operative cooperation with torque tube 218 and cutter 316. More specifically, in FIG. 2 it can be seen that guide wire 110 comprises a main shaft 114 which has a ball-shaped abutment 116 attached at its distal end. Preferably, main shaft 114 is made of stainless steel and abutment 116 is made of a radiopaque 88/12 gold alloy, i.e. the alloy is eighty-eight percent (88%) gold and twelve percent (12%) nickel. Abutment 116 can be attached to main shaft 114 in any manner well known in the art, such as by brazing or molding. Abutment 116 can actually be any of various shapes. For instance, abutment 116 can be either hemispherical or parabolic in its configuration. Regardless of the particular shape, the important structural considerations for abutment 116 are first, that the end be blunt in order to minimize the possibility of inadvertently puncturing an arterial wall as guide wire 110 is being positioned; and second, that abutment 116 be sufficiently large to prevent passage of torque tube 218 and cutter 316 past abutment 116. For example, abutment 116 may be a substantially spherical structure approximately twenty thousandths of an inch (0.020″) in diameter.

A radiopaque helical spring coil 118 surrounds the portion of main shaft 114 which is immediately proximal to abutment 116. Coil 118 acts as a radiopaque marker and as a smooth transitional structure between main shaft 114 and abutment 116. Further, the coil 118 assists in giving the wire 110 a proper flexibility profile. As shown, coil 118 is operatively attached to both abutment 116 and main shaft 114 in a manner to be subsequently disclosed in more detail.

As also shown in FIG. 2, cutter 316 is formed with a hollow cylindrical tip 344, as will be described further below. Tip 344 slidingly surrounds main shaft 114 of guide wire 110. Importantly, although tip 344 can slide along the entire length of main shaft 114, the inner diameter of tip 344 is sufficiently smaller than the outer diameter of ball-shaped abutment 116 to prevent movement of tip 344 past abutment 116.

Figure 3:
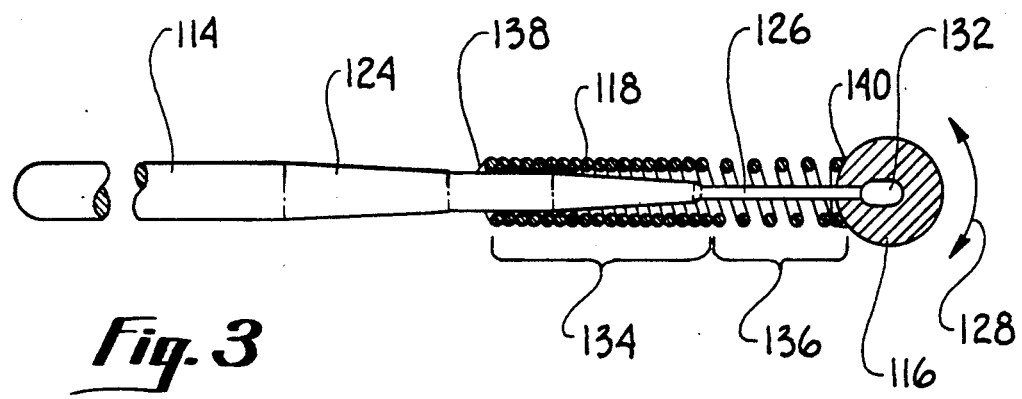
FIG. 3 is a cross-sectional view of the embodiment of the guide wire in FIG. 2 taken along lines 3—3 of FIG. 2.
Figure 4:
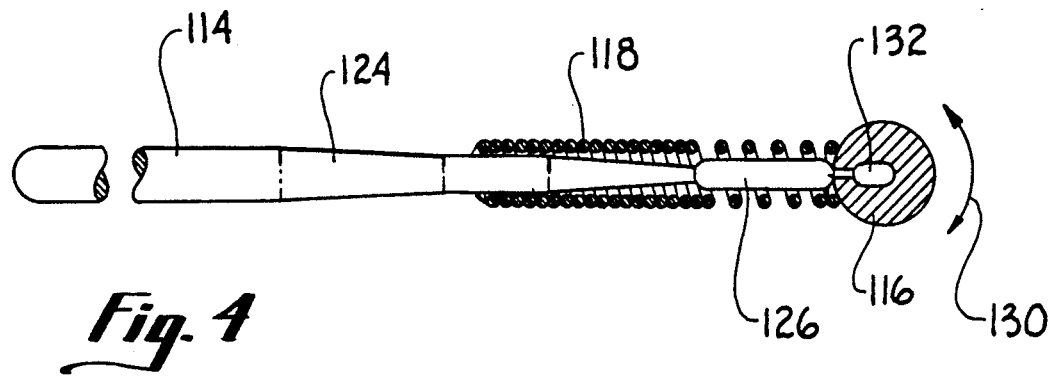
FIG. 4 is a cross-sectional view of the embodiment of the guide wire in FIG. 2 taken along lines 4—4 of FIG. 2.
Figure 10:
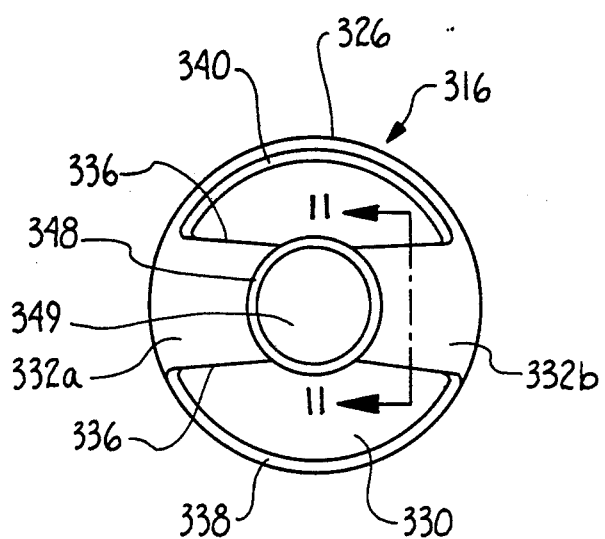
FIG. 10 is an enlarged fragmentary sectional view taken substantially on the lines 10—10 of FIG. 9 and illustrates the construction of the cutter at the front end of the cutter.

Referring now to FIG. 3, it will be seen that main shaft 114 comprises a tapered region 124 which extends from an intermediate point on main shaft 114 toward the distal end of guide wire 110. It is to be understood that the majority of main shaft 114 is proximal to region 124 and is substantially of constant diameter. Within the region 124, the taper of main shaft 114 is substantially uniform with decreasing diameter in the distal direction. Main shaft 114, as it extends distally beyond region 124, is flattened into a ribbon 126 which facilitates the bending of the distal end of guide wire 110 in the directions indicated by arrow 128. On the other hand, from a brief reference to FIG. 4, it will be appreciated by the skilled artisan that ribbon 126 hinders or prevents the bending of the distal end of guide wire 110 in a direction perpendicular to the direction indicated by arrow 128. Specifically, ribbon 126 is intended to limit or prevent the bending of guide wire 110 in the directions indicated by arrow 130 in FIG. 4. Both FIG. 3 and FIG. 4 show that ribbon 126 terminates with a bulb-shaped anchor 132 which provides structure to which the ball-shaped abutment 116 can be securely attached as disclosed above.

Still referring to FIG. 3, it can be seen that wire coil 118 surrounds main shaft 114 in the area immediately proximal to abutment 116. Specifically, coil 118 is a helical spring that is made of a radiopaque 88/12 gold alloy similar to that used for abutment 116 As shown in FIG. 3, coil 118 has a base portion 134 wherein the wire of coil 118 is tightly wound with a low helical pitch to provide some degree of stiffness. Distal to base portion 134, however, is a flexible portion 136 where the wire of coil 118 is not so tightly wound. As shown, flexible portion 136 surrounds ribbon 126 so that the flexibility of ribbon 126 in the directions indicated by arrow 128 is not impaired.

Coil 118 is preferably fixedly attached to main shaft 114 and abutment 116. Specifically, coil 118 may be soldered to main shaft 114 in the taper region 124 at solder connection 138. The end of coil 118 opposite from connection 138 may similarly be brazed onto abutment 116 at braze connection 140 to effectively make coil 118 integral with abutment 116. For emphasis, it is again stated that the outer diameter of coil 118 is sufficiently less than the outer diameter of ball-shaped abutment 116 in order to create a barrier at abutment 116 beyond which cutter 316 cannot proceed.

It will be appreciated by the skilled artisan that the combination of abutment 116 and coil 118 provides a radiopaque marker which can be used by the physician to properly place guide wire 110 within a patient. Further, it will be appreciated that the cooperation between ribbon 126 and flexible portion 136 allows the physician to predictably bend guide wire 110 at a predetermined location in a specifically selected direction to assist in the proper placement of guide wire 110. When once placed, guide wire 110 will be effective for the subsequent placement of torque tube 218 and cutter 316.

FIGS. 5 and 6 illustrate one presently preferred embodiment of the torque tube 218 of atherectomy system 10. As shown, torque tube 218 may include a thin polymeric liner 270 (FIG. 6) made from a suitable material such as a polyamide. However, other suitable polymeric materials may also be used for the liner 270. In one embodiment, liner 270 may have a suitable thickness such as approximately five thousandths of an inch (0.005") and may have a suitable inner diameter such as approximately forty-three thousandths of an inch (0.043").

A wire 272 made from a suitable material, such as tungsten, may be wound spirally on liner 270. Tungsten is desirable because it is strong and resilient and is able to transmit torque, particularly when spirally wound. However, wire 272 may also be made from other suitable materials such as stainless steel, titanium or polymers. In one embodiment, wire 272 may have a suitable diameter such as approximately two thousandths of an inch (0.002") and a tension modulus of approximately 350 Kpsi. Wire 272 may be wound on liner 270 at a suitable angle such as an angle of approximately thirty degrees (30°). It will be appreciated that any resilient member with properties corresponding to those of wire 272 may be used instead of wire 272.

A matrix 274 is disposed on both liner 270 and winding 272 and may be provided with a suitable thickness such as approximately three thousandths of an inch (0.003"). Matrix 274 may be made from a mixture of urethane and epoxy. When such a mixture is cured and subjected to gamma radiation on the order of 2-3 Mrads, matrix 274 becomes three-dimensionally cross-linked. This cross-linking binds matrix 274 to liner 270 and winding 272. The cross-linking enhances the ability of torque tube 218 to provide torque transmission and flexibility. Alternatively, instead of being made from a mixture of urethane and epoxy, the matrix 274 may be made in a manner well known in the art from polymeric composites using glass, boron and/or carbon fibers. The liner 270 and the matrix 274 may be considered as a sheath encasing the wire 272 therebetween.

It will be appreciated that the dimensions specified above for torque tube 218 are only illustrative. Actually, torque tubes of different sizes may be used according to the desires of the operator and incorporated for compatibility when the cutters 316 have different sizes.

One presently preferred embodiment of cutter 316 of atherectomy system 10 is shown in FIGS. 7 through 11. Cutter 316 may be made from a suitable material such as stainless steel. The cutter 316 includes a hollow end portion 326 (FIGS. 7, 8 and 9) having a substantially constant shape such as a cylinder. In one embodiment, the external diameter of the cylindrical portion 326 may be approximately seventy-two thousandths of an inch (0.072"). The thickness of portion 326 may be approximately four thousandths of an inch (0.004") and the length of portion 326 may be approximately one tenth of an inch (0.1"). These dimensions are only illustrative since cutter 316 may be made in different sizes in accordance with the size of the artery in which the cutter is to be received.

An intermediate portion 328 of progressively decreasing dimensions extends from end portion 326. Intermediate portion 328 may have an external length of approximately five hundredths of an inch (0.05") and may constitute a segment of a truncated cone. The diameter of the intermediate portion 328 at the narrow end of the segmented cone may be approximately twenty-two thousandths of an inch (0.022"). As will be appreciated, these dimensions are also only illustrative.

Figure 11:
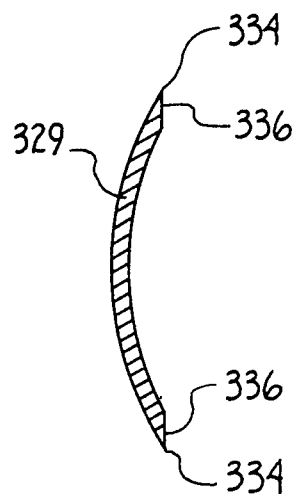
FIG. 11 is a sectional view of the cutter and is taken substantially on the lines 11—11 of FIG. 10.

Intermediate portion 328 is substantially hollow as indicated at 330 in FIGS. 7 and 9. The intermediate portion 328 comprises a pair of diametrically disposed blades 332a and 332b defined by cutting edges 334 (FIG. 11). Cutting edges 334 are preferably quite sharp. The sharpness of cutting edges 334 is enhanced by a progressive tapering (as indicated at 336) at the lateral ends of blades 332 with the distance between the external and internal walls defining the thickness of the blades. The maximum thickness of each of the blades 332 may be on the order of two thousandths to three thousandths of an inch (0.002"-0.003"). Each of the blades 332 preferably has external and internal surfaces with annular configurations. The external and internal surfaces of blades 332 may extend annularly for an angle of approximately fifty degrees (50°) or sixty degrees (60°).

As may be seen by comparing the blades 332 at positions 338 and 340 in FIG. 8, blades 332 are longer at one end than at the other end. The increased length of blades 332 at the position 338 results from a cut made in end portion 326 at a position adjacent the intermediate portion 328. As will be appreciated, the taper in blades 332 at the side adjacent position 338 may be more shallow than the taper of the blades at the side adjacent position 340.

In an atherectomy operation, blades 332 of cutter 316 cut into the obstructive tissue. It happens, however, that the shorter blades 332 at position 340 make a smaller cut into the obstructive tissue than the longer blades 332 at position 338. Thus, the side of cutter 316 on which the shorter blades 332 are located encounters more resistive tissue. The result of this differential cutting is that cutter 316 tends to deflect off its longitudinal axis away from the shorter blades 332 and in the direction of the longer blades. This deflection ensures that the broader sweep of blades 332 is able to cut a channel into the obstructive tissue which has a diameter that is equal to or slightly greater than the diameter of end portion 326. This is necessary in order for cutter 316 to advance into, rather than getting hung up on, the obstructive tissue.

A tip portion 344 extends from intermediate portion 328 of cutter 316. Tip portion 344 has a substantially constant shape at the narrow end of truncated intermediate portion 328. For example, tip portion 344 may be substantially cylindrical. Opening 330 in intermediate portion 328 may, however, extend partially into tip portion 344 as indicated at 346 in FIG. 9. The external diameter of this cylinder may be approximately twenty-three thousandths of an inch (0.023").

A conical portion 348 extends from the cylindrical portion of tip portion 344. The diameter of conical portion 348 at its narrow end may be approximately sixteen thousandths of an inch (0.016"). Conical portion 348 is open at its forward or narrow end as indicated in FIG. 7. The total length of tip portion 344 may be approximately fifteen thousandths to twenty thousandths of an inch (0.015"-0.020"). Blades 332 are integrated at their forward ends by tip portion 344 to impart strength to the blades 332.

In its manufacture, cutter 316 may be initially formed as a unitary body with a solid end portion having the external configuration of end portion 326, a solid conical portion having the external configuration of intermediate portion 328, and a tip portion having the external configuration of tip portion 344. A cylindrical hole may be formed in end portion 326 and in tip portion 344. A hole may also be formed through intermediate portion 328 to connect the cylindrical holes which are respectively formed in end portion 326 and tip portion 344. The intermediate portion 328 is then burned as by electrical discharge machining to form the opening 330 (and the extended opening 346) to define the blades 332.

The structure herein disclosed for cutter 316 allows guide wire 110 to be passed through end portion 326, intermediate portion 328 and tip 344 in a manner which will allow guide wire 110 to guide cutter 316 along a predetermined path. Means to rotate cutter 316 for its intended purpose, such as torque tube 218, can then be operatively attached to cutter 316.

Torque tube 218 and the attached cutter 316 are inserted into the artery 14 of a patient within a flexible protective support sheath 418 and over guide wire 110. Support sheath 418 may be made from a suitable material such as a polyamide and may be coated with a suitable material such as a urethane. However, other polymers may be used instead of a polyamide and other coatings may be used instead of urethane. A control unit 410 is connected to support sheath 418 to control the distance which cutter 316 is permitted to extend beyond the distal end of support sheath 418. One presently preferred embodiment of control unit 410 is the telescopic control unit illustrated in FIGS. 1 and 12.

Figure 12:
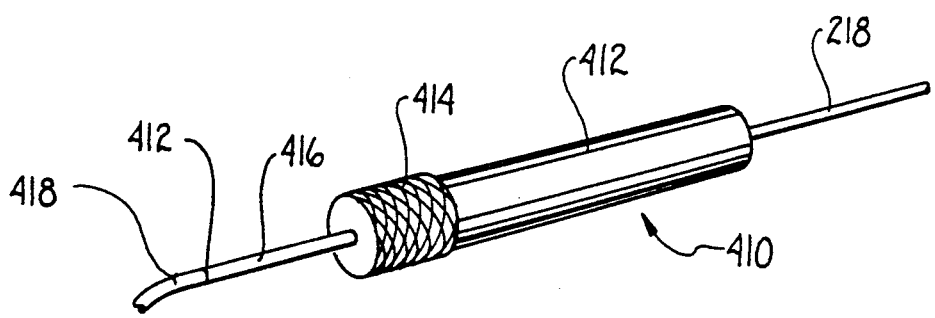
FIG. 12 is a perspective view of one presently preferred embodiment of the support sheath control unit of the atherectomy system of the present invention which is shown in cross-section in FIG. 1.

As shown in FIGS. 1 and 12, control unit 410 comprises a substantially cylindrical-shaped hollow housing 412 having a ring-shaped cap 414 threadably engaged on the distal end thereof for selectively retaining a tube-shaped insert 416 within housing 412. As can be appreciated, as insert 416 is telescopically retracted into housing 412, support sheath 418 is effectively shortened relative to torque tube 218 which thus permits cutter 316 to be correspondingly advanced into the artery 14 of the patient.

Housing 412 of control unit 410 has an interior chamber 424 extending longitudinally between the proximal end and the distal end of housing 412. The proximal end of housing 412 forms an opening 429 through which torque tube 218 can be inserted.

A vacuum source 20 can also be connected to the proximal end of torque tube 218. Vacuum source 20 may be any suitable source of vacuum, such as a standard vacuum bottle. As will be described further below, vacuum source 20 is used to withdraw obstructive tissue cuttings from artery 14 of the patient. Importantly, as can be appreciated by one of skill in the art, removing the obstructive tissue from the artery significantly reduces the likelihood of repeated artery blockage.

In FIG. 1, it can be seen that a ledge 430 is formed at the distal end of housing 412. A ring-shaped cap 414, having a hole 438 therethrough and provided with interior threads 434, is threadably engaged to a plurality of threads 436 formed on the exterior of the distal end of housing 412. Cap 414 preferably has a knurled outer surface, as shown in FIG. 12, for enabling manual engagement and disengagement thereof. As can be appreciated, when cap 414 is connected to housing 412, a gap 437 is formed between ledge 430 of housing 412 and cap 414. An O-ring 432, made of an elastomeric material such as rubber, is positioned within this gap 437.

A tube-shaped insert 416 having a flange 440 at its proximal end is coaxially aligned within housing 412 and is positioned to slide telescopically within chamber 424 of housing 412 through hole 438 in cap 414. When insert 416 is positioned within chamber 424 of housing 412, flange 440 slides along the inside wall of chamber 424 and keeps insert 416 longitudinally aligned within housing 412. In addition, flange 440 eventually abuts O-ring 432 when insert 416 is pulled in a distal direction, thereby preventing complete withdrawal of insert 416 from chamber 424. The distal end 442 of insert 416 is connected to sheath 418 by any one of many methods known in the art, such as by a threaded engagement.

As can be appreciated, when O-ring 432 is in its relaxed position, it has a substantially circular cross-sectional shape. Significantly, in its relaxed position, O-ring 432 does not prevent insert 416 from sliding along its longitudinal axis inside housing 412. On the other hand, as cap 414 is screwed onto housing 412, O-ring 432 is compressed between cap 414 and ledge 430 of housing 412 and is thereby distorted to squeeze against insert 416 to stationarily hold it in a substantially fixed position within housing 412. Thereafter, when cap 414 is unscrewed slightly from housing 412, elastic O-ring 432 returns to its original shape, and insert 416 can again be easily moved with respect to housing 412 along its longitudinal axis.

Advantageously, housing 412 is also provided with a port 426 which extends through housing 412 and into chamber 424. Port 426 is useful for injecting medicinal fluids, as needed, into chamber 424. The fluids in chamber 424 can thus be subsequently introduced through insert 416 and sheath 418 into the artery 14 of the patient to aid in the atherectomy procedure.

OPERATION

When performing an atherectomy operation using the system and method of the present invention, an opening is first made percutaneously at a suitable position such as the groin of the patient. As depicted in FIG. 1, guide wire 110 is then inserted into artery 14 of the patient through the percutaneous opening, and guide wire 110 is advanced along the artery 14 to the position where obstructive tissue such as plaque 12 is to be excised. Actually, guide wire 110 is advanced along artery 14 to a position beyond the obstruction. Cutter 316 and torque tube 218 are then inserted into support sheath 418 and this combination is disposed over guide wire 110 and advanced along guide wire 110 to the position where the obstructive tissue is to be excised from the artery 14.

During the atherectomy procedure, support sheath 418 remains stationary as torque tube 218 is rotated within sheath 418. Significantly, since torque tube 218 is disposed within support sheath 418, torque tube 218 does not rub against the wall of artery 14 when it is rotated.

Referring now to FIG. 13A, cutter 316 is initially positioned within artery 14 such that cutter 316 extends only a short distance from the distal end of support sheath 418. The tip portion 344 of cutter 316 (see FIG. 7) is then advanced into plaque 12 in artery 14, while the torque tube 218 and the cutter 316 are rotating. This rotation may be accomplished manually or automatically as by a motor 22 (see FIG. 1). When a motor 22 is used, it may be operated at a relatively low speed such as approximately eight hundred revolutions per minute (800 rpm). By operating motor 22 at a relatively low speed, the physician is able to more easily control the removal of plaque 12 from the wall of artery 14.

When torque tube 218 is rotated either manually or by motor 22, it transmits torque to the cutter 316. This results from the spiral winding 272 and the cross-linked matrix 274 of torque tube 218 (see FIGS. 5 and 6). The resultant rotation of cutter 316 causes blades 332 of cutter 316 (see FIG. 7) to excise plaque 12 from the wall of artery 14. When small fragments of plaque 12 are excised from the wall of artery 14, they enter opening 330 between the blades 332 of cutter 316. These fragments of plaque 12 are then removed through torque tube 318 by the partial vacuum generated by vacuum source 20 (see FIG. 1).

As is necessary for an atherectomy procedure, when torque tube 218 and the cutter 316 are rotated by the action of drive motor 22, the cutter 316 is incrementally advanced by the physician using various mechanical means at the proximal end of torque tube 218. For example, such advancing means may include the telescopic unit 410 and the slide mechanism 460 shown in cooperation with unit 410 in FIGS. 13A and 13B. First, in order to properly understand the incremental advancement of cutter 316 into artery 14, it is to be appreciated and understood that once sheath 418 is positioned in artery 14, and against the abutment 454 of obstructive plaque 12, the sheath 418 is held stationary. Consequently, insert 416 is also held stationary. With sheath 418 and insert 416 stationarily positioned relative to artery 14, consider telescopic unit 410 to be initially in the configuration shown in FIG. 13A. Also, consider the cutter 316 to be positioned in artery 14 as shown in FIG. 13A.

From its position in FIG. 13A, an advancement of cutter 316 into artery 14 can be accomplished by advancing torque tube 218. As intended here, this can be done with a slide mechanism 460 that is operatively associated with torque tube 218 at a location proximal to the telescopic unit 410 (e.g. on motor drive 22). Specifically, with cross-reference between FIGS. 13A and 13B, the movement of slide mechanism 460 from its position on motor drive 22 as shown in FIG. 13A to its position shown in FIG. 13B results in a corresponding advancement of cutter 316 from its position in FIG. 13A to that shown in FIG. 13B. When, as indicated in FIG. 13B, slide mechanism 460 cannot be advanced any farther on motor drive 22 due to mechanical interactions between slide mechanism 460 and motor drive 22, any more advancement of torque tube 218 and cutter 316 requires that the slide mechanism 460 be repositioned on motor drive 22. As intended here, this can be done by reconfiguring telescopic unit 410.

Reconfiguration of telescopic unit 410 to allow for an additional advancement of torque tube 218 and cutter 316 into artery 14 is accomplished by partially disengaging cap 414 from housing 412. This disengagement relaxes O-ring 432 to loosen its grip on insert 416 and allow advancement of housing 412 over insert 416. If, as intended for the system 10, motor drive 22 is fixedly attached to housing 412 (the actual structure for this connection is not shown) then motor drive 22 will also correspondingly advance relative to insert 416. As shown by a comparison of FIG. 13B with FIG. 13C, this advancement repositions slide mechanism 460 on motor 22 for an additional advancement of torque tube 218 into artery 14. In order to have a complete passageway 452 through plaque 12, the above-described procedure is repeated until a continuous passageway is formed through the plaque 12.

As previously mentioned, a port 426 is preferably provided in housing 412 of control unit 410 for injecting needed medicinal fluids therethrough, such as radiopaque fluids. Such fluids then enter the patient's bloodstream through insert 416 and sheath 418.

Guide wire 110 of atherectomy system 10 is preferably retained in artery 14 throughout the atherectomy operation to guide and support cutter 316. Additionally, because ball-shaped abutment 116 of guide wire 110 has a greater diameter than main shaft 114 of guide wire 110, guide wire 110 mechanically limits the advancement of cutter 316 within artery 14 to that point where cutter 316 makes contact with abutment 116. Another advantage of this cooperation of structure is that when guide wire 110 is withdrawn, cutter 316 and its associated torque tube 218 will be simultaneously withdrawn.

It will be appreciated that the above discussion has been principally confined to the excision of plaque 12 from the arterial walls of a living being. This discussion has been for purposes of explanation. As will be appreciated, the system and method of this invention can be used for excising any obstructive tissue from lumens of living beings without departing from the scope of this invention.

Although this invention has been disclosed and illustrated with reference to particular embodiments, the principles involved are susceptible for use in numerous other embodiments which will be apparent to persons skilled in the art. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. An atherectomy system for excising obstructive tissue from an artery of a patient comprising:
   a guide wire insertable into the artery;
   a support sheath insertable into the artery over the guide wire, the support sheath having a proximal end and a distal end;
   a torque tube having a proximal end and a distal end insertable into the artery through the support sheath over the guide wire;
   a cutter connected to the distal end of the torque tube;
   a substantially cylindrical-shaped hollow housing;
   a tube-shaped insert coaxially aligned and slidingly disposed within said housing, said insert having its distal end connected to said support sheath; and
   a releasable insert holding means mounted on said housing for selectively moving said insert within said housing for selectively controlling the extent to which the cutter on the distal end of the torque tube extends from the distal end of the support sheath.

2. An atherectomy system as defined in claim 1 wherein the guide wire comprises a main shaft having a proximal end and a distal end, and an abutment attached to the distal end of the main shaft to prevent movement of the cutter connected to the torque tube past said abutment.

3. An atherectomy system as defined in claim 1 wherein the torque tube comprises a liner, and a wire wound around the liner.

4. An atherectomy system as defined in claim 1 wherein the cutter comprises:
   a hollow cylindrical base;

a hollow cylindrical tip coaxially distanced from said base; and a hollow frustum coaxially aligned intermediate and respectively attached to said base and said tip, said frustum formed with a first opening to establish a first cutting edge and a second opening to establish a second cutting edge.

5. An atherectomy system as defined in claim 1 further comprising means for withdrawing obstructive tissue cuttings from the artery.

6. An atherectomy system as defined in claim 1 further comprising means for rotating the cutter about the guide wire.

7. An atherectomy system for excising obstructive tissue from an artery of a patient comprising:
   a guide wire insertable into the artery;
   a torque tube having a proximal end and a distal end insertable into the artery over the guide wire;
   a cutter connected to the distal end of the torque tube;
   a support sheath insertable into the artery over the guide wire and the torque tube, the support sheath having a proximal end and a distal end;
   a telescopic control unit having a substantially cylindrical-shaped hollow housing, a tube-shaped insert coaxially aligned and slidingly disposed within said housing, the insert being connected to the proximal end of the support sheath, and a releasable insert holding means mounted on said housing for selectively moving said insert within said housing; and
   means connected to the proximal end of the torque tube for withdrawing obstructive tissue cuttings from the artery.

8. An atherectomy system as defined in claim 7 wherein the means for withdrawing obstructive tissue cuttings comprises a vacuum source.

9. An atherectomy system as defined in claim 7 further comprising means for rotating the torque tube and the cutter about the guide wire.

10. An atherectomy system as defined in claim 9 wherein the rotating means comprises an electric motor.

11. An atherectomy system as defined in claim 9 wherein the guide wire comprises a main shaft having a proximal end and a distal end, and an abutment attached to the distal end of the main shaft to prevent movement of the cutter past said abutment.

12. An atherectomy system as defined in claim 11 wherein said main shaft is formed with a flat ribbon proximal said abutment to bias bending of said main shaft.

13. An atherectomy system as defined in claim 12 further comprising a helically wound wire coil which is positioned in a surrounding relationship over said ribbon, said coil having one end attached to said abutment and an opposite end attached to said main shaft.

14. An atherectomy system as defined in claim 11 wherein the cutter comprises:
   a hollow cylindrical base;
   a hollow cylindrical tip coaxially distanced from said base; and
   a hollow frustum coaxially aligned intermediate and respectively attached to said base and said tip, said frustum formed with a first opening to establish a first cutting edge and a second opening to establish a second cutting edge.

15. An atherectomy system as defined in claim 14 wherein said first opening is larger than said second opening in said frustum to establish said first cutting edge longer than said second cutting edge.

16. An atherectomy system as defined in claim 15 wherein the diameter of said tip of the cutter is less than the diameter of said base of the cutter.

17. An atherectomy system as defined in claim 16 wherein the diameter of said base of the cutter is less than the diameter of said abutment of the guide wire.

18. An atherectomy system as defined in claim 14 wherein the releasable insert holding means of the telescopic control unit comprises a ring-shaped cap threadably engageable with said cylindrical-shaped hollow housing for squeezing an O-ring positioned between said cap and said housing against said tube-shaped insert when said cap is engaged with said housing.

19. An atherectomy system as defined in claim 14 wherein the torque tube comprises a liner and a wire wound around the liner.

20. An atherectomy system as defined in claim 19 wherein the support sheath comprises a polyamide tube which is coated with urethane.

21. A method for excising obstructive tissue from an artery of a patient, the method comprising the steps of:
   (a) positioning a guide wire within the artery;
   (b) positioning a support sheath within the artery over the guide wire, said support sheath having a proximal end attached to a tubular insert;
   (c) sliding said tubular insert into a housing;
   (d) engaging a cap with said housing to prevent motion of said insert relative to said housing;
   (e) positioning a torque tube within the support sheath, the torque tube having a cutter connected to a distal end thereof and the cutter being positioned within the support sheath so as to lie adjacent a distal end of the support sheath;
   (f) positioning the support sheath and the cutter within the artery to bring the cutter into contact with the obstructive tissue;
   (g) cutting the obstructive tissue by rotating the cutter;
   (h) displacing the support sheath in a proximal direction relative to the cutter to a predetermined position;
   (i) rotating the cutter to drill a passageway through said obstruction proportional to the distance of displacement in step (h);
   (j) withdrawing the obstructive tissue from the artery; and
   (k) withdrawing the guide wire, the support sheath, the torque tube, and the cutter from the artery.

22. A method as defined in claim 21 wherein positioning steps (a), (b), and (e) comprise the steps of:
   sliding the guide wire through and past the obstructive tissue in the artery;
   inserting a proximal end of the guide wire through a tip of the cutter;
   positioning the cutter inside the support sheath to provide a slight protrusion of the cutter relative to the support sheath; and
   sliding the support sheath, the cutter, and the torque tube through the artery to come into contact with the obstructive tissue.

23. A method as defined in claim 21 wherein the step of cutting the obstructive tissue by rotating the cutter comprises the steps of:
   connecting an electric motor to the torque tube; and
   actuating the electric motor so as to rotate the torque tube about the guide wire.

24. A method as defined in claim 21 wherein the step of withdrawing the obstructive tissue from the artery comprises the step of connecting a vacuum source to a proximal end of the torque tube.

25. A method as defined in claim 21 wherein the guide wire has an abutment attached to a distal end thereof to prevent movement of the cutter past said abutment and wherein the step of withdrawing the guide wire, the support sheath, the torque tube, and the cutter from the artery comprises the steps of:
displacing the guide wire in a proximal direction relative to the cutter until the abutment on the guide wire engages the cutter; and
withdrawing the guide wire, the cutter, and the torque tube from the artery as a unit.

* * * * *